United States Patent [19]

Norman

[11] 4,229,362
[45] Oct. 21, 1980

[54] ESTERIFICATION PROCESS

[75] Inventor: Paula R. Norman, Midland, Mich.

[73] Assignee: The Dow Chemical Company, Midland, Mich.

[21] Appl. No.: 30,395

[22] Filed: Apr. 16, 1979

[51] Int. Cl.³ .......................... C09F 5/08; C11C 3/00; C07C 67/02; C07C 69/76

[52] U.S. Cl. ..................................... 260/410.6; 560/8; 560/100; 560/112; 560/189; 560/198; 560/199; 560/224; 560/263

[58] Field of Search ...................... 260/410.6; 560/198, 560/199, 263, 224, 189, 100, 112, 8

[56] References Cited

U.S. PATENT DOCUMENTS

| | | | |
|---|---|---|---|
| 2,929,835 | 3/1960 | Hayes | 260/410.6 |
| 3,067,222 | 12/1962 | Anderson | 260/410.6 |
| 3,414,609 | 12/1968 | Hagemeyer | 260/410.6 |
| 3,884,946 | 5/1975 | Sung et al. | 260/410.6 |
| 4,092,339 | 5/1978 | Stevens et al. | 260/410.6 |

Primary Examiner—John F. Niebling
Attorney, Agent, or Firm—David H. Fifield; Douglas N. Deline

[57] ABSTRACT

A process for esterifying terminal hydroxyl groups of a polyoxyalkylene compound comprising one or more ring opened tert.-butyl or tert.-amyl glycidyl ether groups, without removing a significant portion of these tert.-alkyl ether groups. The process is conducted by contacting the polyoxyalkylene compound with an organic, carboxylic acid or anhydride in the liquid phase, in the presence of a small but catalytically effective amount of a Lewis base.

13 Claims, No Drawings

ESTERIFICATION PROCESS

BACKGROUND OF THE INVENTION

The invention is a process for esterifying terminal hydroxyl groups of a polyoxyalkylene compound comprising one or more oxyethylene units bearing on either carbon atom an alkoxy group represented by the formula —CH$_2$OR where R is tert.-butyl or tert.-amyl without removing a significant portion of said R groups.

In U.S. Pat. No. 3,519,559 (1970) polyoxyalkylene compounds similar to those employed in the instant process are reacted with polycarboxylic acids to prepare higher molecular weight polyesters. The only catalyst mentioned therein, in the specific examples of Table II, is p-toluenesulfonic acid (PTSA). In U.S. Pat. No. 3,840,606 dealkylation of tert.-butyl groups from polyoxyalkylene compounds similar to those employed herein is described as occurring in the presence of sulfonic acids under aqueous conditions and in U.S. Pat. No. 4,048,237 a similar reaction is described except under substantially anhydrous conditions.

In U.S. Pat. Nos. 4,003,961 and 4,092,339 at column 5 of each, esterification of the terminal hydroxyls of polyoxyalkylene compounds of this invention is described using acid anhydrides under temperatures of 30°–90° C. or, in the presence of bases, acyl halides, or at higher temperatures with carboxylic acids in the presence of acid catalysts and higher temperatures. It is noted that the presence of strong acids such as aryl sulfonic acids causes simultaneous dealkylation and esterification of the pendant tert.-butoxy groups. Organotin compounds are known to be esterification catalysts for other alcohol/acid reactants.

SUMMARY OF THE INVENTION

An esterification process for esterifying the terminal hydroxyl group(s) of a polyoxyalkylene compound bearing one or more terminal hydroxyl, said compound comprising at least one oxyalkylene unit represented by the formula

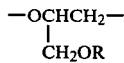

where R represents a tert.-butyl or a tert.-amyl group, without removing a significant portion of the R groups therein, said esterification process comprising contacting, in the liquid phase, said compound with an organic, carboxylic acid or anhydride in the presence of a small but catalytically effective amount of a Lewis base. By using this esterification process, removal of the tert.-butyl or tert.-amyl groups is avoided resulting in a polyoxyalkylene compound esterified only at the terminal end groups or, in the case of esterification by polycarboxylic acids, in polyester compounds having pendant RO- methyl groups along the polyoxyalkylene backbone units. The products are useful as surfactants, lubricants and oil additives.

DETAILED DESCRIPTION OF THE INVENTION

Reactants

The polyoxyalkylene compounds employed as reactants in the instant process are known compounds as noted in U.S. Pat. No. 4,003,961 (column 2 and references cited therein). Generally speaking, they are prepared by polymerizing a tert.-butyl glycidyl ether monomer (hereafter TBGE) or a tert.-amyl glycidyl ether monomer alone or copolymerizing same with one or more other cyclic ethers such as ethylene oxide, 1,2-propylene oxide, 1,2-butylene oxide, trimethylene oxide, tetrahydrofuran, epichlorohydrin, epibromohydrin, 2,2-bis(halomethyl)oxetane or the like. Preferably, R of the polyoxyalkylene compound represents tert.-butyl in the majority of occurrences and more preferably in all occurrences. Preferably, TBGE is copolymerized with one or more 1,2-alkylene oxides, more preferably selected from ethylene oxide; 1,2-propylene oxide; 1,2-butylene oxide; epichlorohydrin and epibromohydrin. Utilization of these monomers will result in one or more oxyethylene; 1,2-oxypropylene; 1,2-oxybutylene; 3-chloro-1,2-oxypropylene; and 3-bromo-1,2-oxypropylene units, respectively, in the polyoxyalkylene compound.

The polyoxyalkylene compound may be initiated from conventional polyoxyalkylene initiators having n active hydrogen atoms which are reactive with alkylene oxides under polymerization conditions. Preferably, the initiator has from one to three active hydrogens which results in a polyoxyalkylene compound comprising one to three terminal hydroxyl groups; most preferably the initiator has one or two active hydrogens which will give a polyoxyalkylene compound having the same number of terminal hydroxyl groups respectively. For example, when initiated off of monohydroxyalcohols, monothiols, or mono- (secondary amines), the polyoxyalkylene compound will comprise one terminal hydroxyl group. When initiated off of difunctional initiators such as glycols and polyglycols, water, bisphenols and the like, the resultant polyoxyalkylene compound will comprise two terminal hydroxyl groups. When a trifunctional initiator such as glycerine or a trialkanolamine is employed as initiator, the final compound will have three terminal hydroxyl groups and so on for tetra-functional and hexafunctional initiators such as pentaerythritol, sorbitol and the like.

The polyoxyalkylene compounds to be employed as reactants are suitably compounds of less than about 20,000 weight average molecular weight, preferably less than about 10,000 and more preferably less than about 7,000 weight average molecular weight, as determined by the standard acetic anhydride-pyridine method for determination of hydroxyl numbers.

Organic Acids and Anhydrides

The organic, carboxylic acid and anhydrides suitable for use in the present process are substantially any carboxylic acid and their respective anhydrides. Dicarboxylic acids and their respective anhydrides may be used to extend the chain length of the backbone of the polyoxyalkylene compound. Polycarboxylic acids and respective anhydrides of functionality greater than two, even when used in small amounts, quickly cross-link and gel the polymer, hence they are ordinarily used in very small amounts, if at all. Because α,β-unsaturated carboxylic acids, such as acrylic and methacrylic acid, tend to polymerize at temperatures above about 100° C., it is generally undesirable to employ them in the reaction process. Since linear products are ordinarily desired, mono- and dicarboxylic acids are preferred in the invention as are polyoxyalkylene compounds having no more than two terminal hydroxyl groups.

The preferred carboxylic acids are the monocarboxylic acids, most preferably saturated and unsaturated aliphatic monocarboxylic acids and aromatic monocarboxylic acids. Saturated and unsaturated fatty, monocarboxylic acids comprising eight to about fifty carbon atoms, such as hexanoic, heptanoic, octanoic, decanoic, lauric, stearic, oleic, linoleic, myristic, and the like. The aromatic acids such as benzoic, alkylbenzoic and naphthoic acids are also a preferred class.

Catalysts

The catalysts to be employed in the present invention are Lewis bases, defined as compounds which contain an unshared pair of electrons with which such compounds can form a coordinate covalent bond with other atoms. Included are such compounds as the amines, mono-, di- and tri- aliphatic and alkanol amines, pyridines, piperidines, aromatic amines, ammonia, ureas, quinolines, imidazoles and imidazolines and other heterocyclic nitrogen compounds and the like. Examples include aniline, triethylene diamine, imidazole, piperidine, pyrrolidine and diethanolamine. Another class of such Lewis bases are organometallic compounds such as dibutyl tin oxide, monobutyl tin chloride, triphenyl phosphine and other organometallic compounds with unshared electron pairs such as metal carbonyls and phosphine or phosphite complexes, e.g. iron pentacarbonyl. Especially preferred are the organo-tin Lewis bases, more specifically dibutyl tin oxide and monobutyl tin chloride, and the N-substituted tetra(lower alkyl) ureas, more specifically N,N,N',N'-tetramethyl urea.

Reaction Conditions

The present process is suitably carried out at temperatures above about 100° C., preferably above about 130° C., more preferably above about 140° C. and suitably below about 250° C., preferably below about 230° C. and more preferably below about 200° C. The reaction may be carried out at atmospheric pressure or the autogenous pressure of the system or it may be carried out under a vacuum to accelerate esterification.

The reactants are contacted at the reaction temperature for any suitable length of time and generally two to eight hours will be sufficient. Depending on the degree of esterification desired, more or less contact at the reaction temperature may be employed. The degree of esterification can be followed and controlled by measuring the disappearance of hydroxyl groups by analyzing an aliquot from time to time as the reaction progresses by NMR analysis, by acid titration or by determination of water generated in the esterification process.

The reactants are suitably contacted in about a 1.5:1 or less acid to hydroxyl equivalent ratio, preferably in about a 1:1 or less acid to hydroxyl equivalent ratio. When chain extension is desired by the formation of polyesters, utilization of an acid to hydroxyl equivalent ratio of about unity is preferable.

The amount of Lewis base catalyst to be employed is a small but catalytically active amount which is suitably less than about 5 weight percent based on the weight of reactants. Preferably, the amount of catalyst is less than about 2 weight percent, more preferably less than about 1 weight percent and is preferably greater than about 0.025 weight percent, more preferably greater than about 0.05 weight percent. More catalyst may, of course, be used but because catalysts in excess of the catalytic amount is wasted, it will be preferable from an economic standpoint to use only as much a necessary to catalyze the reaction and this can be easily determined by minimal routine experimentation.

SPECIFIC EMBODIMENTS OF THE INVENTION

Example 1. Dibutyl tin oxide catalyst

In a stirred, three-necked flask equipped with a thermometer, a Dean-Stark trap and a condenser attached to a vacuum pump with a methylene chloride/dry ice trap, a charge of about 82.5 parts by weight of a polyoxyalkylene compound is contacted with about 11.8 parts by weight lauric acid and 0.47 parts by weight dibutyl tin oxide catalyst (0.5 weight percent catalyst based on reactants). The polyoxyalkylene compound is a 90/10 mole percent ethylene oxide/TBGE copolymer of about 1,400 weight average molecular weight, initiated on ethylene glycol. The reaction mixture is heated with energy supplied by an IR lamp to about 140° C. for one hour at atmospheric pressure and then for an additional two hours at a vacuum of less than about 5 mm Hg. The product (warm) is almost clear and colorless and cools to a white, semi-solid. Titration with 0.1 N sodium hydroxide reveals 95 percent conversion of lauric acid to the ester. Analysis of the product with NMR spectroscopy demonstrates that less than 1 percent of the tert.-butyl groups have been removed during the esterification.

Example 2. Triphenylphosphine catalyst

As in Example 1, a polyoxyalkylene compound is contacted with myristic acid in about a 1:1 acid to hydroxyl equivalent ratio in the presence of 0.5 weight percent, based on reactants, of triphenylphosphine. The mixture is heated at about 150° C. for 1.5 hours under atmospheric pressure and then for 1.5 additional hours at vacuum of less than about 5 mm Hg. Titration of the reaction mixture indicates that conversion of about 36 percent takes place with no substantial dealkylation of the tert.-butyl groups from the product. The polyoxyalkylene reactant employed is a 70/30 mole percent ethylene oxide/TBGE copolymer initiated on water, of about 1,200 weight average molecular weight.

Example 3. Urea catalyst

As in Examples 1 and 2, about equivalent amounts of linoleic acid and a polyoxyalkylene compound are contacted in toluene in the presence of about 0.5 weight percent, based on reactants, of N,N,N',N'-tetramethylurea. The polyoxyalkylene compound is a 70/20/10 mole percent ethylene oxide/1,2-propylene oxide/TBGE terpolymer initiated on glycerine, of about 5,000 weight average molecular weight. The reaction mixture is heated to maintain a brisk toluene reflux for about 7 hours. Analysis indicates that approximately 96 percent conversion of acid to the ester has occurred with no significant dealkylation of the tert.-butyl groups.

Example 4. Quinoline catalyst

In the foregoing fashion, equivalent amounts of lauric acid and a polyoxyalkylene compound are contacted in the presence of about 0.5 weight percent, based on reactants, quinoline. The polyoxyalkylene compound is a 80/20 mole percent ethylene oxide/TBGE copolymer initiated on water, of about 4,000 weight average molecular weight. The reactants are heated to about 150°

C. for 2.5 hours at atmospheric pressure, then 1.5 hours at 200 mm Hg and then 1.5 hours at 150 mm Hg. Analysis of an aliquot reveals about 19 percent conversion of acid to ester. Continued heating at 150 mm hg for an additional 5 hours results in a total conversion of about 36 percent with no significant dealkylation of the tert.-butyl groups.

I claim:

1. A process for esterifying terminal hydroxyl group(s) of a polyoxyalkylene compound bearing one or more terminal hydroxyl, said compound comprising at least one oxyalkylene unit represented by the formula

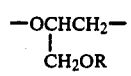

where R represents a tert.-butyl or a tert.-amyl group, without removing a significant portion of the R groups therein, said process comprising contacting, in the liquid phase, said compound with an organic, carboxylic acid or anhydride in the presence of a small but catalytically effective amount of a Lewis base.

2. The process of claim 1 wherein R represents tert.-butyl.

3. The process of claim 2 wherein the polyoxyalkylene compound further comprises one or more units selected from oxyethylene; 1,2-oxypropylene; 1,2-oxybutylene; 3-chloro-1,2-oxypropylene; and 3-bromo-1,2-oxypropylene.

4. The process of claim 2 wherein the polyoxyalkylene compound comprises from 1 to 3 terminal hydroxyl group(s).

5. The process of claim 2 wherein said polyoxyalkylene compound has a weight average molecular weight of about 10,000 or less.

6. The process of claim 2 wherein said Lewis base is selected from organo tin compounds and amine compounds.

7. The process of claim 6 wherein said Lewis base is dibutyl tin oxide.

8. The process of claim 2 wherein said compound and Lewis base are contacted at a temperature of about 110° C. to about 250° C.

9. The process of claim 2 wherein said compound is contacted with an organic, monocarboxylic acid.

10. The process of claim 9 wherein said acid is selected from saturated and unsaturated aliphatic acids and aromatic acids.

11. The process of claim 10 wherein said acid is selected from saturated and unsaturated aliphatic acids.

12. The process of claim 2 wherein the polyoxyalkylene compound comprises from 1 to 3 terminal hydroxyl groups and has a weight average molecular weight of about 10,000 or less, the acid is selected from saturated and unsaturated fatty, monocarboxylic acids, the Lewis base is dibutyl tin oxide and the compound and Lewis base are contacted at a temperature between about 130° C. and about 230° C.

13. The process of claim 2 wherein said Lewis base is triphenyl phosphine.